(12) United States Patent
Kim (10) Patent No.: US 10,732,119 B2
(45) Date of Patent: Aug. 4, 2020

(54) BIOCHIP FOR MEASURING BLOOD GLUCOSE LEVELS, AND BLOOD GLUCOSE METER FOR SMARTPHONE, CONTAINING SAME

(71) Applicant: GACHON UNIVERSITY INDUSTRY ACADEMIC COOPERATION FOUNDATION, Seongnam-si, Gyeonggi-Do (KR)

(72) Inventor: Sanghyo Kim, Yongin-si (KR)

(73) Assignee: GACHON UNIVERSITY INDUSTRY ACADEMIC COOPERATION FOUNDATION, Seongnam-si (KR)

(*) Notice: Subject to any disclaimer, the term of this patent is extended or adjusted under 35 U.S.C. 154(b) by 706 days.

(21) Appl. No.: 14/902,289

(22) PCT Filed: Jul. 8, 2013

(86) PCT No.: PCT/KR2013/006023
§ 371 (c)(1),
(2) Date: Dec. 30, 2015

(87) PCT Pub. No.: WO2015/005504
PCT Pub. Date: Jan. 15, 2015

(65) Prior Publication Data
US 2016/0131590 A1 May 12, 2016

(51) Int. Cl.
*G01N 21/78* (2006.01)
*A61B 5/145* (2006.01)
(Continued)

(52) U.S. Cl.
CPC ......... *G01N 21/78* (2013.01); *A61B 5/14532* (2013.01); *A61B 5/6898* (2013.01);
(Continued)

(58) Field of Classification Search
CPC .......... G01N 21/78; G01N 2021/7759; G01N 21/8483; G01N 33/525; G01N 33/66; A61B 5/6898; A61B 5/14532
See application file for complete search history.

(56) References Cited

U.S. PATENT DOCUMENTS 5,306,623 A    4/1994   Kiser et al.
5,948,695 A *   9/1999   Douglas ................ B01L 3/5023
                                                                     422/401

(Continued)

FOREIGN PATENT DOCUMENTS

JP               10010125 A      1/1998
KR      1020020088521 A    11/2002
(Continued)

OTHER PUBLICATIONS

International Search Report of PCT/KR2013/006023, dated Apr. 9, 2004 (English Translation).

*Primary Examiner* — Samuel P Siefke
(74) *Attorney, Agent, or Firm* — STIP Law Group, LLC (57) ABSTRACT

Disclosed are a biochip for measuring blood glucose levels and a blood glucose meter for a smartphone including the same. The biochip for measuring blood glucose levels includes: a substrate, one surface of which is provided with a blood glucose inflow region into which blood glucose flows and with a reaction region that is connected to the blood glucose inflow region and has a recess formed therein, a porous separator disposed on the blood glucose inflow region to face the surface of the substrate, and silica nanoparticles and a reaction reagent distributed on the reaction region of the substrate. Thereby, blood glucose levels can be measured using such a biochip, which is easy to carry, together with a CMOS image sensor, and particularly, blood glucose levels can be simply measured using a CMOS image sensor provided to a smartphone, and blood glucose levels (Continued)

can be quantitatively measured and checked using a blood glucose meter application installed on a smartphone.

18 Claims, 7 Drawing Sheets

(51) Int. Cl.
  *G01N 33/52*  (2006.01)
  *A61B 5/00*  (2006.01)
  *G01N 33/66*  (2006.01)
  *G01N 21/84*  (2006.01)
  *G01N 21/77*  (2006.01)

(52) U.S. Cl.
  CPC ....... *G01N 21/8483* (2013.01); *G01N 33/525* (2013.01); *G01N 33/66* (2013.01); *G01N 2021/7759* (2013.01)

(56) References Cited

U.S. PATENT DOCUMENTS

| | | |
|---|---|---|
| 2008/0274565 A1 | 11/2008 | Samake et al. |
| 2011/0070634 A1 | 3/2011 | Takahashi et al. |
| 2014/0273271 A1* | 9/2014 | Aizawa ............ G01N 33/54373 436/501 |

FOREIGN PATENT DOCUMENTS

| | | |
|---|---|---|
| KR | 1020070006304 A | 1/2007 |
| KR | 100808415 B1 | 2/2008 |

* cited by examiner

BIOCHIP FOR MEASURING BLOOD GLUCOSE LEVELS, AND BLOOD GLUCOSE METER FOR SMARTPHONE, CONTAINING SAME

This is a U.S. national stage application of PCT Application No. PCT/KR2013/006023 under 35 U.S.C. 371, filed Jul. 8, 2013 in Korean, which is hereby incorporated by reference.

TECHNICAL FIELD

The present invention relates to a biochip for measuring blood glucose levels and, more particularly, to a biochip for measuring blood glucose levels, which may quantitatively measure blood glucose levels based on changes in color intensity depending on the reaction between blood glucose and a reaction reagent, and a blood glucose meter for a smartphone including the same.

BACKGROUND ART

Recently, the number of patients who suffer from diabetes, which is typically regarded as an adult disease, is continuously increasing. Accordingly, there is great interest and demand for techniques for measuring the blood glucose levels of diabetic patients.

However, conventional blood glucose meters, which adopt a biological enzyme manner, are problematic in that the use thereof is cumbersome because an enzyme sensor has to be exchanged at intervals of two or three days. Also, the blood glucose meters are difficult to manufacture due to the complicated structure thereof, and are also difficult to carry owing to the large volume thereof.

In the real world, there is an urgent need for technology for measuring blood glucose levels characterized by increased user friendliness while still realizing the accurate and reliable real-time measurement of blood glucose levels.

DISCLOSURE

Technical Problem

Accordingly, an object of the present invention is to provide a biochip for measuring blood glucose levels, which has a simple configuration and is thus easy to carry, and which enables the real-time measurement of blood glucose levels, and also to provide a blood glucose meter for a smartphone, which may measure the glucose levels of blood fed into a biochip using a CMOS image sensor, which is conventionally attached to a smartphone, and enables the quantitative measurement of blood glucose levels using a blood glucose measurement application installed on a smartphone.

Technical Solution

An aspect of the present invention provides a biochip for measuring blood glucose levels, comprising: a substrate, one surface of which is provided with a blood glucose inflow region into which blood glucose flows and with a reaction region that is connected to the blood glucose inflow region and has a recess formed therein; a porous separator disposed on the blood glucose inflow region to face the surface of the substrate; and silica nanoparticles and a reaction reagent distributed on the reaction region of the substrate.

The biochip may further comprise a cap member disposed on the reaction region of the substrate.

The cap member may have a protrusion, and the convex portion of the protrusion and the concave portion of the recess may be lined up and oriented away from each other to form a space therebetween.

The recess may accommodate blood glucose and may constitute a photon detection region.

The space may accommodate blood glucose and may constitute a photon detection region.

The porous separator may comprise at least one selected from the group consisting of nitrocellulose, polysulfone, polyester, polyamide, polyimide, polyamideimide, poly (meta-phenylene isophthalamide), polyetherketone, polyetherimide, polyethylene, polypropylene, polyvinylidene fluoride, perfluoropolymer, polyvinyl chloride, polyvinylidene chloride, polyethylene glycol derivatives, polyoxide, polyvinylacetate, polystyrene, polyacrylonitrile, polymethylmethacrylate, and non-woven fabrics.

The silica nanoparticles may be functionalized with a hydrophilic functional group.

The hydrophilic functional group may comprise at least one selected from the group consisting of an amine group, a carboxyl group, a hydroxyl group, and a thiol group.

The silica nanoparticles may have a diameter of 10 to 300 nm.

The reaction reagent may comprise glucose oxidase and chromogen.

The glucose oxidase may comprise glucose oxidase immobilized to the silica nanoparticles.

The chromogen may be any one selected from the group consisting of 2,2'-azino-bis(3-ethylbenzothiazoline-6-sulphonic acid), O-dianisidine, 0-toluidine-blue, potassium iodide, tetramethyl benzidine, meta[3-methyl-2-benzothiazolinonehydrazone]N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G, and auramine O-anhydrous.

The reaction reagent may further comprise peroxidase.

The substrate may further comprise a blood glucose absorption region that is connected to the reaction region in the direction away from the blood glucose inflow region of the substrate, and the biochip may further comprise an absorption member disposed on the blood glucose absorption region.

The substrate and the cap member may have light transmissivity.

The substrate and the cap member may each independently comprise at least one selected from the group consisting of polyester, polyacrylate, polyethylene (PE), polypropylene (PP), polysulfone (PS), polyethersulfone (PES), polycarbonate (PC), polyarylate (PAR), polyimide (PI), polyamide, and glass.

The biochip may include at least one selected from among a first adhesive member disposed between the substrate and the cap member, and a second adhesive member disposed between the cap member and the porous separator, the first adhesive member may have therein a through-hole corresponding to the blood glucose inflow region, the reaction region, and the blood glucose absorption region, and the second adhesive member may have therein a blood glucose through-hole corresponding to the blood glucose inflow region so as to pass blood glucose therethrough.

One end of the cap member may not overlap with all or a portion of the blood glucose through-hole of the second adhesive member.

The biochip may further comprise a pad member disposed on the porous separator.

Another aspect of the present invention provides a blood glucose meter, comprising: a biochip for measuring blood glucose levels, comprising a substrate, one surface of which is provided with a blood glucose inflow region into which blood glucose flows and with a reaction region that is connected to the blood glucose inflow region and has a recess formed therein, a porous separator disposed on the blood glucose inflow region to face the surface of the substrate, and silica nanoparticles and a reaction reagent distributed on the reaction region of the substrate; and a CMOS image sensor for measuring the number of photons that pass through the biochip.

The number of photons may be the number of photons passing through the recess, which is a photon detection region of the biochip.

The CMOS image sensor may be provided to a smartphone.

The smartphone may include an application for quantitatively displaying the number of photons measured by the CMOS image sensor.

The application may quantitatively display a blood glucose concentration using a database that correlates the blood glucose concentration with the number of photons passing through the biochip.

Advantageous Effects

According to embodiments of the present invention, blood glucose levels can be simply measured using a biochip for measuring blood glucose levels, which is easy to carry, and a CMOS image sensor. In particular, blood glucose levels can be conveniently measured, regardless of time or place, using a blood glucose meter for a smartphone including a CMOS image sensor, and the quantitative real-time monitoring of blood glucose levels is possible by means of an installed blood glucose measurement application.

BEST MODE

The present invention may be modified in various forms and may have a variety of embodiments, and specific embodiments are illustrated in the appended drawings and are described in detail in the specification. However, the following description does not limit the present invention to the specific embodiments, and should be understood to include all variations, equivalents or substitutions within the spirit and scope of the present invention. Furthermore, descriptions of known techniques, even if they are pertinent to the present invention, are considered unnecessary and may be omitted insofar as they would make the characteristics of the invention unclear.

As used herein, the terms "first," "second," etc. may be used to describe various elements, but these elements should not be limited by these terms. These terms are only used to distinguish one element from another element.

The terms used herein are merely intended to explain specific examples and not to limit the present invention. Unless otherwise stated, the singular expression includes a plural expression. In this application, the terms "include" or "have" are used to designate the presence of features, numbers, steps, operations, elements, parts or combinations thereof described in the specification, and should be understood as not excluding the presence or additional possibility of one or more different features, numbers, steps, operations, elements, parts or combinations thereof.

Hereinafter, a detailed description will be given of embodiments of the present invention, with reference to the appended drawings. Throughout the drawings, the same reference numerals are used to designate the same or similar elements, and the redundant description thereof will be omitted.

Figure 1:
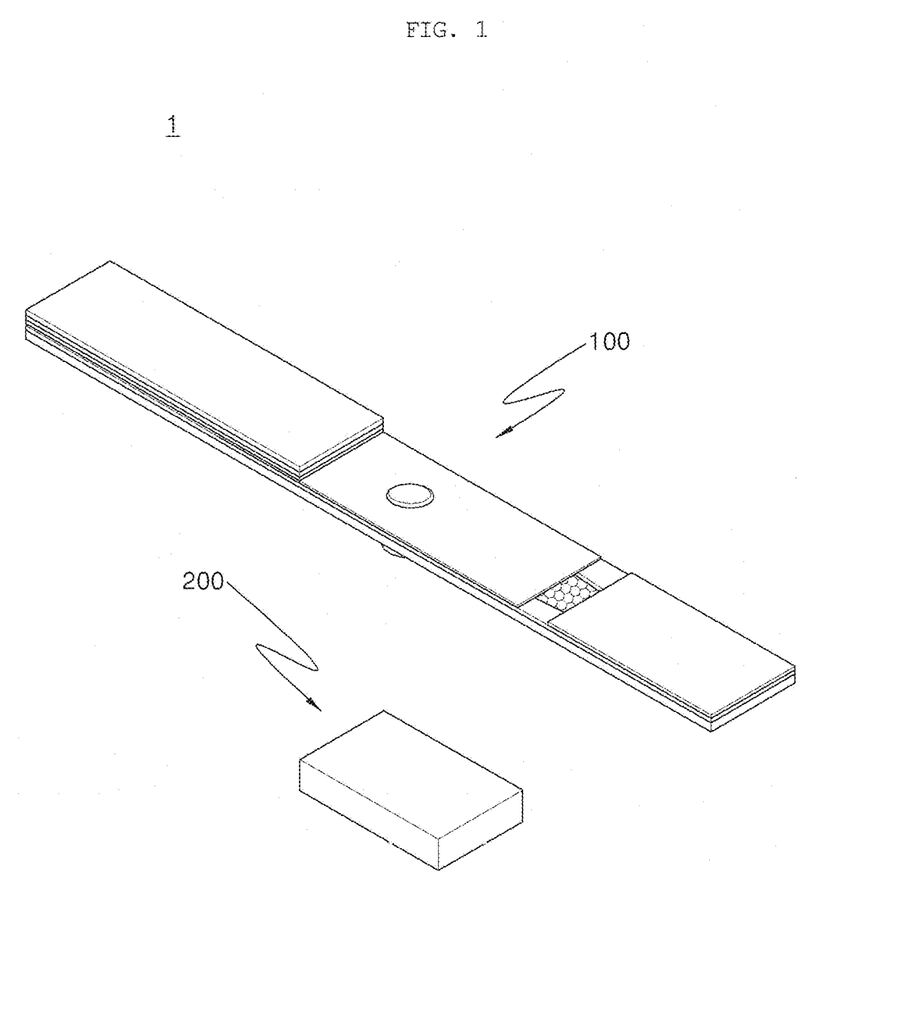
FIG. 1 schematically illustrates a blood glucose meter according to an embodiment of the present invention.
Figure 2:
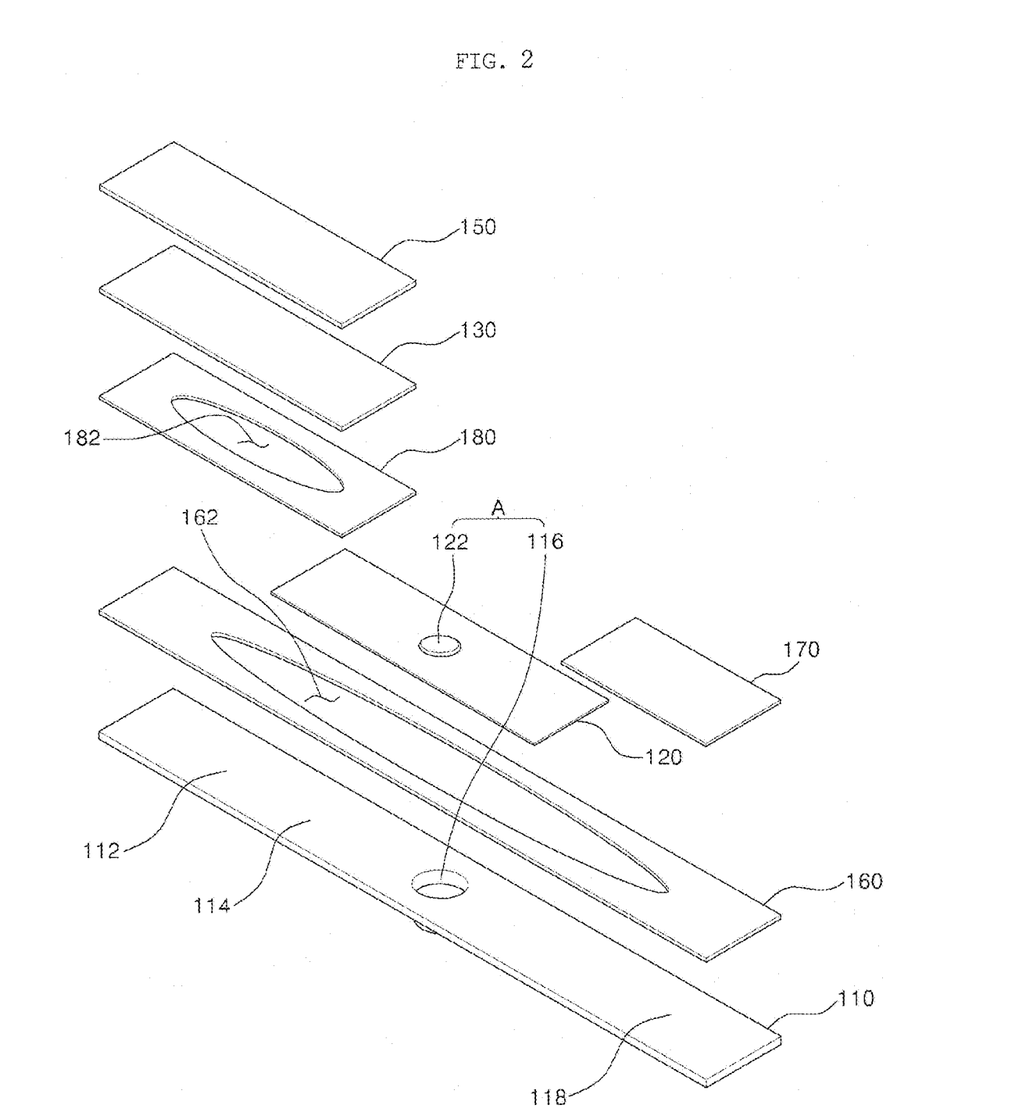
FIG. 2 is an exploded perspective view illustrating the biochip for measuring blood glucose levels before the introduction of silica nanoparticles and a reaction reagent, according to an embodiment of the present invention.
Figure 3:
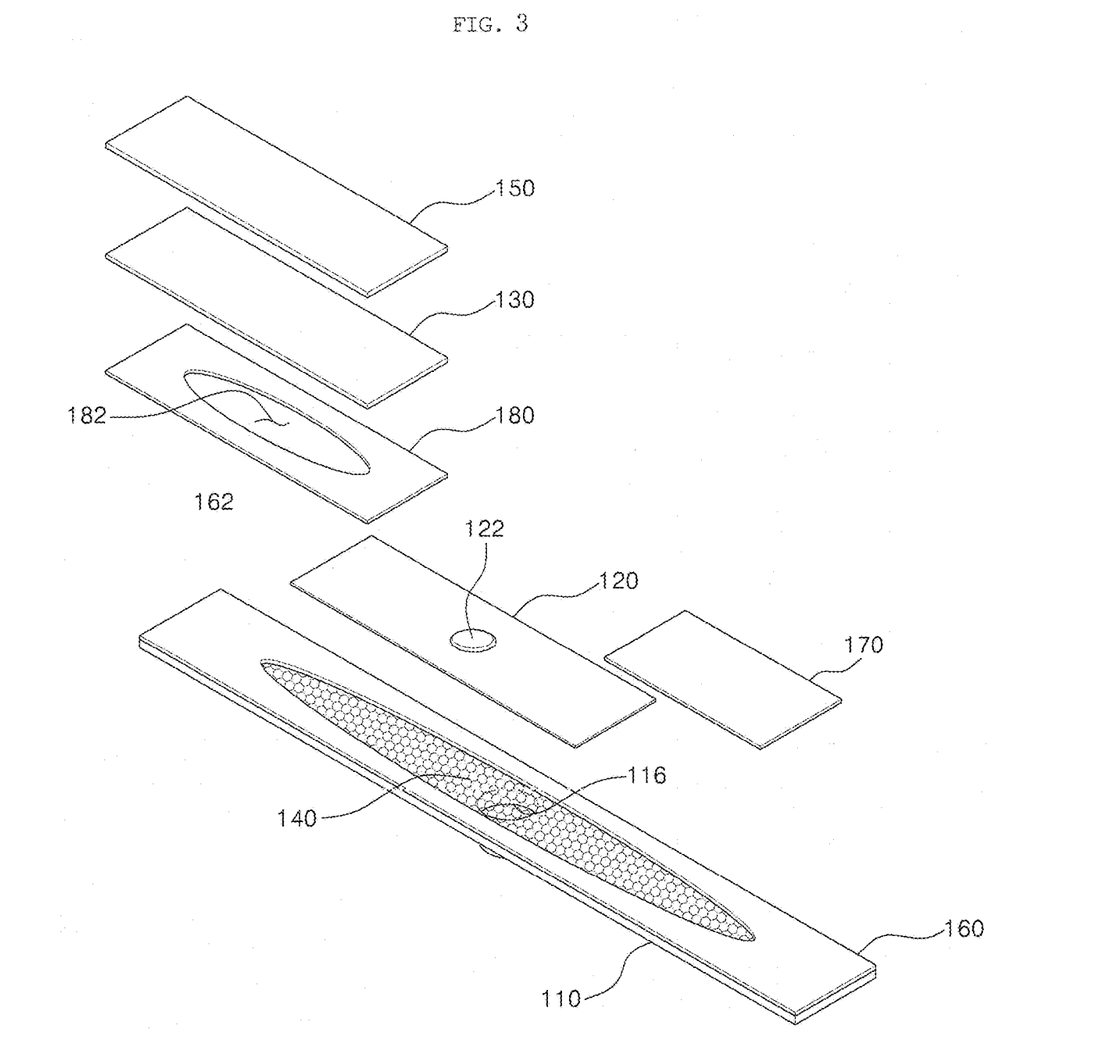
FIG. 3 is an exploded perspective view illustrating the biochip for measuring blood glucose levels after the introduction of silica nanoparticles and a reaction reagent, according to an embodiment of the present invention.

FIG. 1 schematically illustrates a blood glucose meter according to an embodiment of the present invention, FIG. 2 is an exploded perspective view illustrating the biochip for measuring blood glucose levels according to an embodiment of the present invention before the introduction of amine-functionalized silica nanoparticles having a reaction reagent immobilized thereto, and FIG. 3 is an exploded perspective view illustrating the biochip for measuring blood glucose levels according to an embodiment of the present invention, after the introduction of the silica nanoparticles and the reaction reagent.

With reference to FIG. 1, which schematically illustrates the configuration of the blood glucose meter 1 according to the embodiment of the present invention, the blood glucose meter 1 includes a biochip 100 for measuring blood glucose levels and a CMOS image sensor 200.

The transmittance of light through the biochip 100 for measuring blood glucose levels is measured using a CMOS image sensor 200, particularly a CMOS image sensor 200 provided to a smartphone (not shown), thereby realizing the rapid and effective measurement of blood glucose levels.

With reference to FIGS. 2 and 3, the biochip 100 for measuring blood glucose levels according to an embodiment of the present invention includes a substrate 110, one surface of which is provided with a blood glucose inflow region 112, into which blood glucose flows, and with a reaction region 114 that is connected to the blood glucose inflow region 112 and has a recess 116 formed therein; a porous separator 130 disposed on the blood glucose inflow region 112 to face the surface of the substrate 110; and silica nanoparticles and a reaction reagent 140 distributed on the reaction region 114 of the substrate 110.

The substrate 110 is preferably made of a light-transmitting material.

Examples of the material for the substrate 110 may include polyester, polyacrylate, polyethylene (PE), polypropylene (PP), polysulfone (PS), polyethersulfone (PES), polycarbonate (PC), polyarylate (PAR), polyimide (PI), polyamide, and glass, which may be used alone or in combinations of two or more. Preferably useful is polyester, but the present invention is not limited thereto.

The blood glucose inflow region 112 and the reaction region 114, which is connected thereto, are provided on one surface of the substrate 110. The reaction region 114 may be formed to extend in a direction away from the blood glucose inflow region 112, and the blood glucose inflow region 112 and the reaction region 114 are continuously connected to each other, with no visible boundary therebetween. Hence, these regions may overlap in some sections.

As such, the recess 116, which is able to receive a predetermined amount of plasma containing blood glucose, may be formed at a portion of the reaction region 114. The recess 116 may constitute a photon detection region A together with a protrusion 122 on a cap member 120, which will be described below. The photon detection region A is specified below.

When the blood to be measured is fed into the biochip 100 for measuring blood glucose levels according to an embodiment of the present invention, it may pass through the porous separator 130, and the plasma component containing blood glucose, except for biopolymers including blood cells and proteins, may flow into the blood glucose inflow region 112 and may then be transferred into the reaction region 114. The silica nanoparticles and the reaction reagent 140 are distributed on the reaction region 114. The blood may be whole blood.

The cap member 120 may be additionally disposed on the reaction region 114 of the substrate 110, and is preferably composed of a light-transmitting material, like the substrate 110.

The material for the cap member 120 may include any of the above-noted examples of the material for use in the substrate 110.

The cap member 120 may have a protrusion 122 formed at a position corresponding to the recess 116 of the substrate 110, and the convex portion of the protrusion 122 and the concave portion of the recess 116 are lined up and oriented away from each other to thereby form a space therebetween.

The space accommodates a portion of the plasma containing blood glucose, which is fed into the reaction region 114, and the number of photons in the light that passes through this space is detected by the CMOS image sensor 200. Hence, the region defined by the recess 116 and the protrusion 122 may constitute the photon detection region A.

In the case where the cap member 120 is not used, the photon detection region A may be composed exclusively of the recess 116. Preferably, the photon detection region A is formed by coupling the recess 116 with the protrusion 122.

When the photon detection region A is provided in this way, the plasma containing blood glucose that reacts with the reaction reagent may be stably accommodated, and the thickness of the photon detection region A is ensured by the sum of the depth of the recess 116 and the height of the protrusion 122, whereby light transmittance depending on the color intensity therein may be accurately applied to the sensor. Furthermore, the reaction time may be shortened, and the accuracy of light detection in the light detection region is assured.

The porous separator 130 is disposed at a position corresponding to the blood glucose inflow region 112 of the substrate 110, and functions as a filter for filtering biopolymers, including blood cells and proteins, from the whole blood including all components of the blood sample.

As necessary, a pad 150 is additionally provided on the porous separator 130 so as to directly accommodate and primarily filter the blood sample for measuring blood glucose. The pad 150 may be made of glass fiber, a membrane, etc., but the present invention is not limited thereto. The membrane may include nitrocellulose, polysulfone, polyester, polyamide, polyimide, polyamideimide, poly(meta-phenylene isophthalamide), polyetherketone, polyetherimide, polyethylene, polypropylene, polyvinylidene fluoride, perfluoropolymer, polyvinyl chloride, polyvinylidene chloride, polyethylene glycol derivatives, polyoxide, polyvinylacetate, polystyrene, polyacrylonitrile, and polymethylmethacrylate, which may be used alone or in combinations of two or more.

As illustrated in FIGS. 2 and 3, the porous separator 130, which is disposed at one side of the substrate 110, may function to couple the cap member 120 to the substrate 110 by interposing one end of the cap member 120 between the porous separator 130 and the substrate 110.

Examples of the material for the porous separator 130 may include nitrocellulose, polysulfone, polyester, polyamide, polyimide, polyamideimide, poly(meta-phenylene isophthalamide), polyetherketone, polyetherimide, polyethylene, polypropylene, polyvinylidene fluoride, perfluoropolymer, polyvinyl chloride, polyvinylidene chloride, polyethylene glycol derivatives, polyoxide, polyvinylacetate, polystyrene, polyacrylonitrile, polymethylmethacrylate, and non-woven fabrics.

The silica nanoparticles and the reaction reagent 140 are disposed on the reaction region 114 of the substrate 110, and the silica nanoparticles are preferably functionalized with a hydrophilic functional group.

Examples of the hydrophilic functional group may include an amine group, a carboxyl group, a hydroxyl group, and a thiol group. Preferably useful is an amine group.

The amine group, carboxyl group, and thiol group are each independently C1-C30, preferably C1-C20, more preferably C1-010, and much more preferably C1-C6.

The amine group may include a primary amine group ($-NH_2$) or a secondary amine group ($-NRH$), and is preferably a primary amine group, wherein R is an alkyl group.

Unless otherwise defined, the term "alkyl" used herein refers to a linear, branched or cyclic aliphatic hydrocarbon group. The alkyl group may be a saturated alkyl, including no double bonds or triple bonds. Alternatively, the alkyl group may be an unsaturated alkyl, including at least one double or triple bond. The alkyl group may be a C1-C14 alkyl group. More specifically, the alkyl group may be a C1-C10 alkyl group or a C1-C6 alkyl group.

For example, the C1-C4 alkyl group may be an alkyl chain having 1 to 4 carbon atoms, and the alkyl chain may be selected from the group consisting of methyl, ethyl, propyl, iso-propyl, n-butyl, iso-butyl, sec-butyl, and t-butyl.

Specific examples of the alkyl group may include a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, and a cyclohexyl group.

The reaction reagent 140 may include glucose oxidase and chromogen. Herein, chromogen may function as a dye that exhibits a predetermined color intensity depending on the amount of blood glucose. The chromogen is provided in the form of reduced chromogen, which is colorless, and the color intensity of chromogen may vary depending on the kind thereof based on the extent of oxidation thereof. Briefly, the color of chromogen becomes dark with an increase in the extent of oxidation thereof.

Any one or more of the reaction reagent and chromogen may be immobilized to hydrophilic functional group-functionalized silica nanoparticles due to electrostatic attraction.

The hydrophilic functional group-functionalized silica nanoparticles may help improve the performance of the biochip 100 for measuring blood glucose levels. Typically, silica nanoparticles exhibit chemical stability, thermal stability, and biocompatibility.

Since the silica nanoparticles are hydrophilic, the plasma containing blood glucose is allowed to flow uniformly and rapidly in the reaction region having the silica nanoparticles distributed thereon so that blood glucose may be accurately and quickly measured. Preferably, when the hydrophilicity of the silica nanoparticles is increased through functionalization with a hydrophilic functional group, blood glucose levels may be measured more accurately and quickly.

The silica nanoparticles have a diameter smaller than the wavelength of visible light, preferably 10 to 300 nm, more preferably 70 to 200 nm, and much more preferably 50 to 100 nm. If the diameter of the silica nanoparticles is less than 10 nm, workability may be deteriorated. In contrast, if the diameter thereof exceeds 300 nm, light transmissivity may decrease.

The chromogen may include 2,2'-azino-bis(3-ethylbenzothiazoline-6-sulphonic acid), O-dianisidine, 0-toluidine-blue, potassium iodide, tetramethyl benzidine, meta[3-methyl-2-benzothiazolinonehydrazone]N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G, and auramine O-anhydrous.

In the reaction reagent, the weight ratio of the glucose oxidase relative to the chromogen is 0.01 to 40, preferably 0.05 to 20, and more preferably 0.1 to 10. If the weight ratio thereof is less than 0.01, the rate of oxidation of blood glucose may decrease. In contrast, if the Weight ratio thereof exceeds 40, the increase in the rate of oxidation of blood glucose may become insignificant.

The reaction reagent may further include peroxidase. The peroxidase may function as a catalyst for promoting the oxidation of chromogen.

The weight ratio of the peroxidase relative to the glucose oxidase is 0.01 to 10, preferably 0.05 to 5, and more preferably 0.1 to 2. If the weight ratio of the peroxidase relative to the glucose oxidase is less than 0.01, the rate of oxidation of chromogen may decrease. In contrast, if the weight ratio thereof exceeds 10, the increase in the rate of oxidation of chromogen may become insignificant.

Changes in color intensity depending on the reaction between blood glucose and glucose oxidase and the oxidation of 2,2'-azino-bis(3-ethylbenzothiazoline-6-sulphonic acid) (ABTS) may be represented by the following Schemes 1 and 2 below.

[Scheme 1]

[Scheme 2]

As shown in Schemes 1 and 2, when glucose contained in the blood reacts with glucose oxidase, hydrogen peroxide ($H_2O_2$) is produced, and colorless ABTS turns green while being oxidized through the reaction with hydrogen peroxide, and the green color of ABTS becomes increasingly dark with an increase in the extent of oxidation thereof.

Also, a blood glucose absorption region may be further provided at the portion of the substrate that is connected to the reaction region 114 in the direction away from the blood glucose inflow region 112 of the substrate 110, and an absorption member 170 may be further provided on the blood glucose absorption region. When the plasma containing blood glucose is introduced in a large amount, a portion of the plasma is absorbed into the absorption member 170 via the reaction region 114, thus preventing the plasma from leaking out of the biochip 100 for measuring blood glucose levels.

The biochip 100 for measuring blood glucose levels according to the present embodiment may further include a first adhesive member 160 and a second adhesive member 180, which are interposed between the substrate 110 and the porous separator 130.

Specifically, the first adhesive member 160 may be interposed between the substrate 110 and the cap member 120, and the second adhesive member 180 may be interposed between the cap member 120 and the porous separator 130.

The first adhesive member 160 may include a through-hole 162 corresponding to the blood glucose inflow region 112, the reaction region 114 and the blood glucose absorption region 118, and the second adhesive member 180 may include a blood glucose through-hole 182 through which the blood glucose passes.

The first and second adhesive members 160, 180 may be formed using an adhesive film or an adhesive.

With reference to FIG. 1, the blood glucose meter 1 according to the present embodiment includes a biochip 100 for measuring blood glucose levels and a CMOS image sensor 200.

The biochip 100 for measuring blood glucose levels remains the same as in the above description, and a detailed description thereof is omitted.

The CMOS image sensor (CIS) 200 functions to detect an optical signal that is then converted into a digital electrical signal, may be operated simply, and may be implemented so as to achieve scanning in a variety of manners, and a signal processing circuit may be integrated into a single chip, thus enabling the fabrication of a small product. Since the CMOS processing technique is compatible, manufacturing costs may be decreased and power consumption is very low, and thus the CMOS image sensor may be easily applied to products having limited battery capacity.

The principle of the CMOS image sensor 200 is as follows. A single photodiode in the sensor is responsible for absorbing light and converting it into another kind of signal. This procedure depends on the photoelectric effect. When photons are accumulated in the form of an electric charge and converted from electrons, the amount thereof is proportional to the number of photons that are detected through contact with the CMOS image sensor. The accumulated electric charges are amplified in analog voltage form and may then be converted into digital numbers. The numbers displayed on the digital output are proportional to the number of photons detected by the image sensor. If the passage of photons is blocked by the presence of any material on the surface of the image sensor, the output digital number may decrease.

In the present embodiment, visible light may be used as a light source, but the present invention is not limited thereto.

The CMOS image sensor may be provided to a smartphone (not shown) or a camera (not shown). In particular, when the blood glucose is measured using the CMOS image sensor 200 of a smartphone, rapid and effective measurement become possible.

Specifically, an application for quantitatively displaying the number of photons may be installed on a smartphone equipped with such a CMOS image sensor.

Also, samples having various blood glucose concentrations are ensured, and a database correlating blood glucose concentration with the measured number of photons is constructed, and may then be applied to the application. When the application is operated, the blood sample is placed in the biochip and allowed to react, and the number of photons detected by the CMOS image sensor may be directly displayed in the blood glucose concentration.

Such an application may also be embedded in a camera provided with a CMOS image sensor.

MODE FOR INVENTION

Preparation Example 1: Preparation of Reaction Reagent Solution 5 mg of glucose oxidase (100,000 units/g) was added to 2.5 mL of purified water, thus preparing a glucose oxidase solution. 5 mg of peroxidase (300 units/g) was added to 2.5 mL of purified water, thus preparing a peroxidase solution. 20 mg of ABTS was added to 1 mL of purified water to give a 35 mM ABTS solution.

All of the prepared solutions were stored in a refrigerator until use. The glucose oxidase solution, the peroxidase solution and the ABTS solution were mixed at a volume ratio of 2:2:1, thus preparing a reaction reagent solution.

Preparation Example 2: Preparation of Amine-Functionalized Silica Nanoparticles 6.16 mL of ammonia was mixed with 0.5 mL of aminopropyltriethoxysilane and then added to 6.95 mL of ethanol and 4.48 mL of purified water, and the resulting mixture was stirred for 1 hr. Subsequently, 2.5 mL of tetraethoxysilane was added, thus obtaining the titular nanoparticles.

Preparation Example 3: Preparation of Mixture Comprising Amine-Functionalized Silica Nanoparticles and Reaction Reagent 1 mg of the amine-functionalized silica nanoparticles of Preparation Example 2 was added to 0.1 mL of the reaction reagent solution of Preparation Example 1 and mixed together, thus preparing a mixture comprising the reaction reagent and the amine-functionalized silica nanoparticles having the reaction reagent immobilized thereto.

The amine-functionalized silica nanoparticles are regarded as important in the biochip for measuring blood glucose levels. Typically, silica nanoparticles exhibit chemical stability, optical transparency, low-temperature encapsulation, thermal stability, and biocompatibility. In particular, glucose oxidase and chromogen may be immobilized to an amine-functionalized silica substrate due to electrostatic attraction.

Preparation Example 4: Manufacture of Biochip for Measuring Blood Glucose Levels With reference to FIGS. 1 to 3, a method of manufacturing the biochip for measuring blood glucose levels according to the present invention is described below.

Specifically, hydrophilic PET (polyethylene terephthalate) film, a sample pad made of a glass fiber membrane, a plasma separation membrane, double-sided adhesive tape, and an absorption pad were prepared.

At the center of a substrate 110 comprising a hydrophilic PET film (width×length×thickness=24×8×0.1 mm), a circular recess 116, corresponding to the detection region A, having a diameter of 4 mm and a depth of 0.2 mm, was formed on the reaction region 114 using a press.

Subsequently, 15 μL of the mixture 140 comprising the analytical reagent and the amine-functionalized silica nanoparticles having the reaction reagent immobilized thereto, obtained in Preparation Example 3, was fed into the reaction region 114 of the substrate 160, coated thereon in an oval shape with a diameter of 15 mm in a transverse direction, and then stored in a refrigerator until use.

The first piece of double-sided tape (width×length×thickness=24×8×0.1 mm) 160 having the through-hole 162 in the center thereof was disposed on the substrate so that the four corners thereof were aligned with the four corners of the substrate 110.

Next, on the center of a top layer (width×length×thickness=10×8×0.1 mm) 120 made of a hydrophilic PET film, a circular protrusion 122 having a diameter of 3 mm and a height of 0.2 mm was formed using a press, and the top layer 120 was disposed on the substrate 110 so that the concave portion of the substrate and the convex portion of the top layer were lined up and oriented away from each other to form a space therebetween, and the end of the first piece of double-sided tape 160 was interposed therebetween, thereby coupling the substrate 110 with the top layer 120. This space was designated as the photon detection region A.

The absorption pad (width×length×thickness=8×8×0.1 mm) 170 made of cellulose fibers having high absorption capacity was attached to the end of the substrate having the blood glucose absorption region 118 connected to the reaction region 114 in the direction away from the blood glucose inflow region 112 of the substrate 110, whereby an excess of plasma was absorbed.

Next, one end of the plasma separation membrane (width×length×thickness=6×8×0.1 mm) 130 was overlapped with one end of the top layer 120, and the second piece of double-sided tape (width×length×thickness=6×8×0.1 mm) was interposed between the top layer and the first piece of double-sided adhesive tape to adhere the plasma separation membrane. Here, the corners of the plasma separation membrane were disposed so as to be aligned with the corners of the substrate.

The second piece of double-sided adhesive tape had a blood glucose through-hole having a diameter of 3 mm in the center thereof. As such, the sample pad 150 and the absorption pad 170 were adhered so as to be aligned with the corners of the substrate 110 in order to prevent the leakage of the blood sample and to function as a packing. Each of the first and second pieces of double-sided adhesive tape had a through-hole in the center thereof so as not to interfere with the passage of blood glucose or the transmission of light.

Test Example

Figure 4:
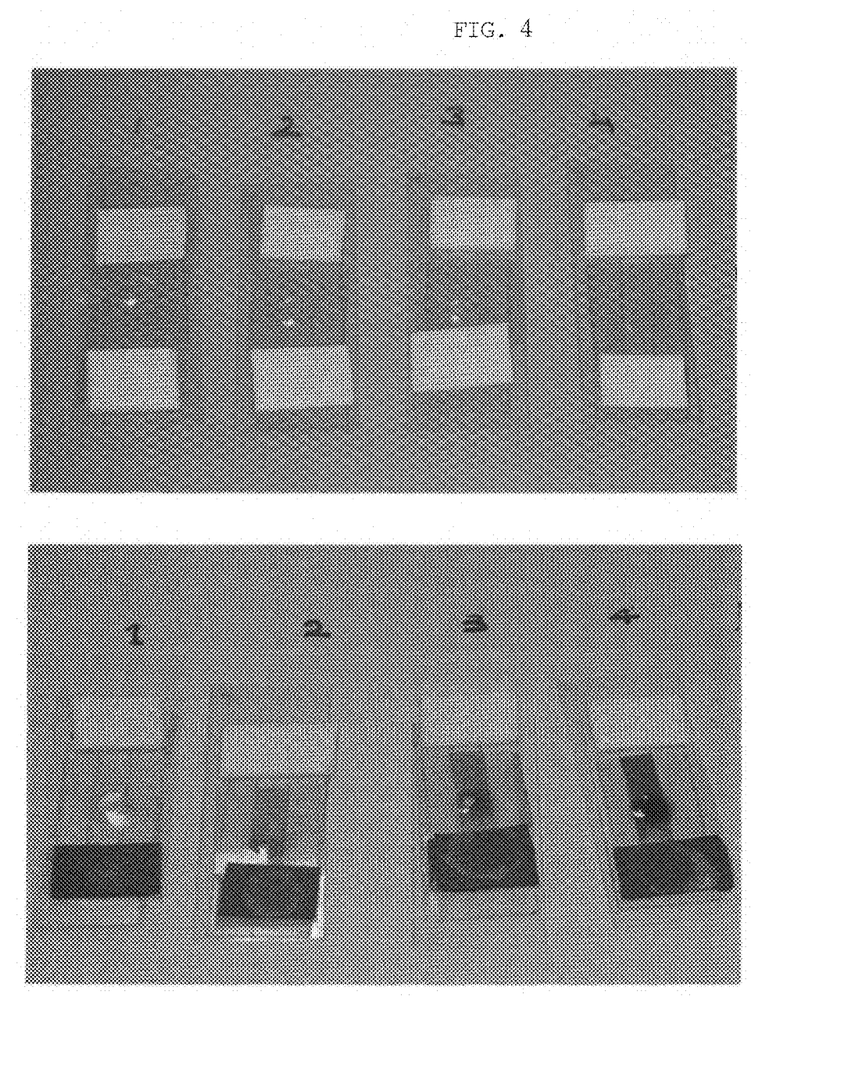
FIG. 4 illustrates the biochips for measuring blood glucose levels according to the present invention, before and after the reaction in the measurement of blood glucose levels using four blood samples having different blood glucose concentrations.

Analysis of Relationship Between Blood Glucose Concentration and Number of Photons FIG. 4 illustrates the biochips for measuring blood glucose levels before and after the reaction in the measurement of blood glucose using four blood samples having different blood glucose concentrations (Sample 2, Sample 7, Sample 14, and Sample 24, moving rightwards).

With reference to FIG. 4, as the blood glucose concentration was higher, the green color of the detection region became darker.

Blood containing blood glucose at various concentrations was sampled from a mouse and a high-fat diet (HFD) mouse at various time intervals after feeding of ipGTT. The samples were taken from the mouse after fasting for 5 hr and 20 hr, and were also taken 0 min, 15 min, 30 min, 60 min, 120 min, and 140 min after feeding. Also, the samples were taken from the HFD mouse 0 min, 30 min, 90 min, 120 min and 160 min after feeding, thus preparing 28 blood samples.

The glucose concentrations of the prepared blood samples were measured using a GM 9 blood glucose analyzer and an Accu-check point-of-care blood glucose sensor, and the 28 blood samples were fed into the biochip for measuring blood glucose levels according to the present invention so that the blood glucose and the reaction reagent were reacted for 3 min, and the number of photons passing through the biochip for measuring blood glucose levels was measured using the CMOS image sensor. The photons were analyzed using a NOON0PC30L, 110000 active single chip CMOS image sensor.

The results of analysis of the blood glucose concentration and the number of photons are shown in Table 1 below and in FIG. 5.

TABLE 1

| Sample No. | Blood glucose concentration (μg/mL) | | Number of photons (A.U.) by CMOS SENOR |
|---|---|---|---|
| | GM9 | Accu-Check | |
| 1 | 110 | 102 | 161 |
| 2 | 131 | 126 | 159 |
| 3 | 163 | 153 | 146 |
| 4 | 178 | 149 | 143 |
| 5 | 183 | 165 | 143 |
| 6 | 193 | 178 | 139 |
| 7 | 246 | 216 | 121 |
| 8 | 249 | 183 | 119 |
| 9 | 262 | 258 | 115 |
| 10 | 269 | 283 | 115 |
| 11 | 291 | 301 | 106 |
| 12 | 308 | 261 | 100 |
| 13 | 316 | 321 | 94 |
| 14 | 321 | 299 | 87 |
| 15 | 330 | 317 | 85 |
| 16 | 366 | 369 | 73 |
| 17 | 378 | 367 | 70 |

TABLE 1-continued

| Sample No. | Blood glucose concentration (μg/mL) | | Number of photons (A.U.) by CMOS SENOR |
|---|---|---|---|
| | GM9 | Accu-Check | |
| 18 | 380 | 351 | 67 |
| 19 | 388 | 385 | 58 |
| 20 | 416 | 450 | 50 |
| 21 | 437 | 421 | 45 |
| 22 | 443 | 427 | 44 |
| 23 | 448 | 469 | 45 |
| 24 | 452 | 415 | 45 |
| 25 | 472 | 467 | 37 |
| 26 | 491 | 515 | 36 |
| 27 | 494 | 484 | 36 |
| 28 | 586 | 548 | 31 |

Figure 5:
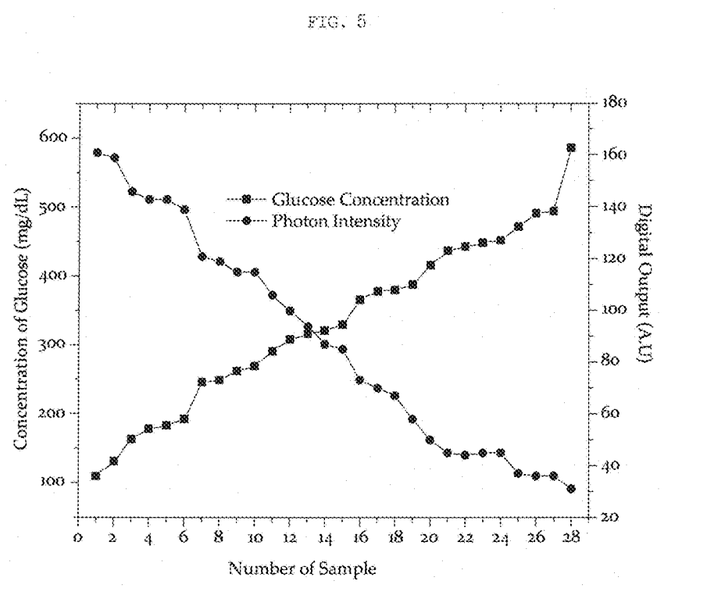
FIG. 5 is a graph illustrating the relationship between the concentration of blood glucose and the number of photons that pass through the biochip for measuring blood glucose levels according to the present invention.

With reference to Table 1 and FIG. 5, as the blood glucose concentration increased, the number of photons that were measured decreased. This is because the color of the photon detection region of the biochip for measuring blood glucose levels becomes darker with an increase in the blood glucose concentration, thus lowering the light transmittance.

Figure 6:
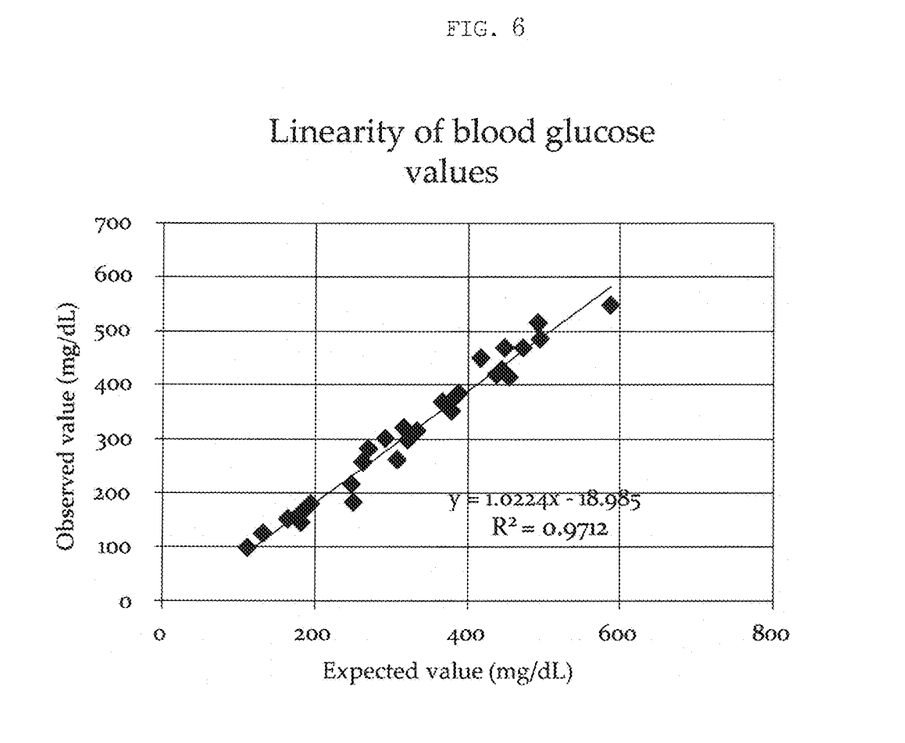
FIG. 6 is a graph illustrating the linearity between the expected value and the observed value of the blood glucose concentration using the biochip for measuring blood glucose levels according to the present invention.
Figure 7:
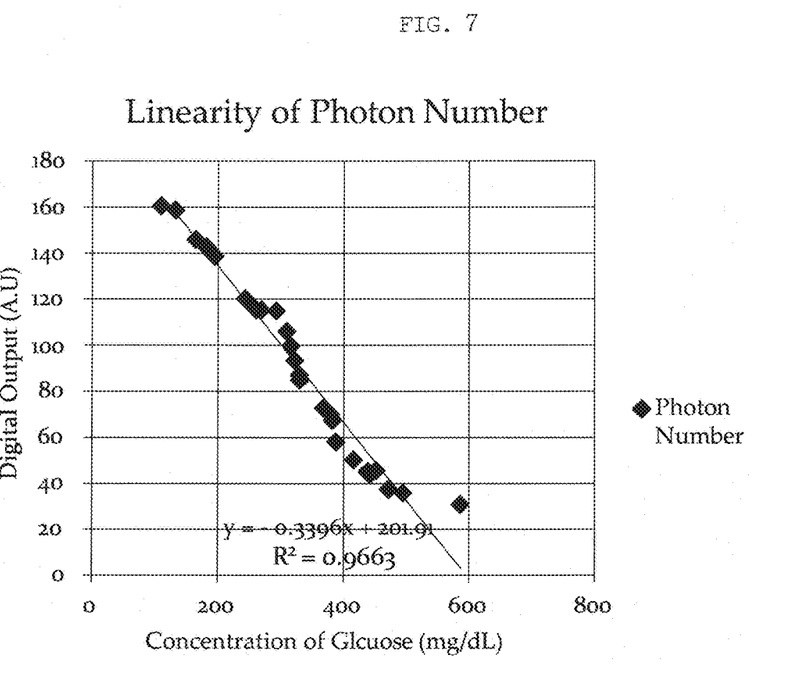
FIG. 7 is a graph illustrating the linearity between the blood glucose concentration, measured using the blood glucose meter according to the present invention, and the digital output for the number of photons.

In FIG. 6, the expected value on the transverse axis represents the glucose concentration measured by GM9, and the observed value on the longitudinal axis represents the glucose concentration measured by the Accu-Check instrument. In FIG. 7, the glucose concentration on the transverse axis is the blood glucose concentration measured by GM9.

With reference to FIGS. 6 and 7, the linearity on the glucose concentration graph between GM9 and Accu-Check was 0.9712, and the linearity on the photon number graph was 0.9663. In the case where these test results were databased, when blood to be measured is dropped on the biochip for measuring blood glucose levels so as to count the number of photons, the glucose content of the corresponding blood sample may be measured in real time. When such results are utilized in the smartphone application, simple and accurate measurement of blood glucose is possible.

Although the preferred embodiments of the present invention have been disclosed for illustrative purposes, those skilled in the art will appreciate that various modifications and alterations are possible through the addition, change of deletion of elements, without departing from the scope and spirit of the invention as disclosed in the accompanying claims.

INDUSTRIAL APPLICABILITY

According to embodiments of the present invention, blood glucose can be simply measured using a biochip for measuring blood glucose levels, which is easy to carry, and a CMOS image sensor. In particular, blood glucose levels can be conveniently measured, regardless of time or place, using a blood glucose meter for a smartphone including a CMOS image sensor, and blood glucose levels can be quantitatively checked in real time using the installed blood glucose measurement application.

The invention claimed is:

1. A biochip for measuring blood glucose levels, comprising:
    a substrate, one surface of which is provided with a blood glucose inflow region into which blood glucose flows and with a reaction region that is connected to the blood glucose inflow region and has a recess formed therein;
    a porous separator disposed above the blood glucose inflow region to face the surface of the substrate; and silica nanoparticles and a reaction reagent distributed on the reaction region of the substrate,
wherein the recess accommodates the blood glucose and constitutes a photon detection region.

2. The biochip of claim 1, further comprising a cap member disposed on the reaction region of the substrate.

3. The biochip of claim 2, wherein the cap member has a protrusion, and a convex portion of the protrusion and a concave portion of the recess are lined up and oriented away from each other to form a space therebetween.

4. The biochip of claim 3, wherein the space accommodates blood glucose and constitutes a photon detection region.

5. The biochip of claim 1, wherein the porous separator comprises at least one selected from the group consisting of nitrocellulose, polysulfone, polyester, polyamide, polyimide, polyamideimide, poly(meta-phenylene isophthalamide), polyetherketone, polyetherimide, polyethylene, polypropylene, polyvinylidene fluoride, perfluoropolymer, polyvinyl chloride, polyvinylidene chloride, polyethylene glycol derivatives, polyoxide, polyvinylacetate, polystyrene, polyacrylonitrile, polymethylmethacrylate, and non-woven fabrics.

6. The biochip of claim 1, wherein the silica nanoparticles are functionalized with a hydrophilic functional group.

7. The biochip of claim 6, wherein the hydrophilic functional group comprises at least one selected from the group consisting of an amine group, a carboxyl group, a hydroxyl group, and a thiol group.

8. The biochip of claim 1, wherein the silica nanoparticles have a diameter of 10 to 300 nm.

9. The biochip of claim 1, wherein the reaction reagent comprises glucose oxidase and chromogen.

10. The biochip of claim 9, wherein the glucose oxidase comprises glucose oxidase immobilized to the silica nanoparticles.

11. The biochip of claim 9, wherein the chromogen is any one selected from the group consisting of 2,2'-azino-bis(3-ethylbenzothiazoline-6-sulphonic acid), O-dianisidine, O-toluidine-blue, potassium iodide, tetramethyl benzidine, meta[3-methyl-2-benzothiazolinonehydrazone] N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G, and auramine O-anhydrous.

12. The biochip of claim 9, wherein the reaction reagent further comprises peroxidase.

13. The biochip of claim 1, wherein the substrate further comprises a blood glucose absorption region that is connected to the reaction region in a direction away from the blood glucose inflow region of the substrate, and the biochip further comprises an absorption member disposed on the blood glucose absorption region.

14. The biochip of claim 1, wherein the substrate and the cap member have light transmissivity.

15. The biochip of claim 1, wherein the substrate and the cap member each independently comprise at least one selected from the group consisting of polyester, polyacrylate, polyethylene (PE), polypropylene (PP), polysulfone (PS), polyethersulfone (PES), polycarbonate (PC), polyarylate (PAR), polyimide (PI), polyamide, and glass.

16. The biochip of claim 13, wherein the biochip includes at least one selected from among a first adhesive member disposed between the substrate and the cap member, and a second adhesive member disposed between the cap member and the porous separator,
the first adhesive member has therein a through-hole corresponding to the blood glucose inflow region, the reaction region, and the blood glucose absorption region, and
the second adhesive member has therein a blood glucose through-hole corresponding to the blood glucose inflow region so as to pass blood glucose therethrough.

17. The biochip of claim 16, wherein one end of the cap member does not overlap with all or a portion of the blood glucose through-hole of the second adhesive member.

18. The biochip of claim 1, further comprising a pad member disposed on the porous separator.

* * * * *